United States Patent [19]

Farina et al.

[11] Patent Number: 5,750,061
[45] Date of Patent: May 12, 1998

[54] HALOHYDANTOIN FORMS PRODUCED BY MELT EXTRUSION AND METHOD FOR MAKING

[75] Inventors: Thomas Edward Farina, Flemington; Kenneth Scott Geick, Mercerville; Julia Anne Falter, Glen Gardner, all of N.J.

[73] Assignee: Lonza Inc., Fair Lawn, N.J.

[21] Appl. No.: 645,798

[22] Filed: May 16, 1996

Related U.S. Application Data

[63] Continuation-in-part of Ser. No. 554,476, Nov. 7, 1995, abandoned.

[51] Int. Cl.$^6$ .................... B29B 9/10; B29B 9/02
[52] U.S. Cl. ............... 264/117; 264/118; 264/141; 264/211.11; 264/211.23; 510/192; 548/311.7; 548/317.1
[58] Field of Search .................... 264/141–143, 264/118, 122, 211.11, 117, 211.23; 252/103, 99, 102; 548/309.1, 311.7, 317.1; 424/464, 76.7; 510/192, 382, 390; 4/227.1, 227.7

[56] References Cited

U.S. PATENT DOCUMENTS

| | | | |
|---|---|---|---|
| 3,803,285 | 4/1974 | Jensen | 264/12 |
| 4,418,030 | 11/1983 | Muller et al. | 264/143 |
| 4,560,766 | 12/1985 | Girard et al. | 264/122 |
| 4,713,079 | 12/1987 | Chun et al. | 8/101 |
| 5,281,351 | 1/1994 | Romeo et al. | 252/99 |
| 5,565,576 | 10/1996 | Hall et al. | 548/317.1 |

FOREIGN PATENT DOCUMENTS

| | | |
|---|---|---|
| 0 206 725 | 12/1986 | European Pat. Off. |
| WO 92/03532 | 3/1992 | WIPO . |
| WO 94/12612 | 6/1994 | WIPO . |

*Primary Examiner*—Jeffery R. Thurlow
*Attorney, Agent, or Firm*—Darby & Darby

[57] ABSTRACT

The present invention is a method for producing solid halogenated hydantoin products using the process of melt extrusion. The form of the products which can be produced includes tablets, briquettes, pucks, dispensers, "designer" forms such as Christmas ornaments, pellets, and granules. The halogenated hydantoin compounds used in the forms contain methylethylhydantoin or an admixture of methylethylhydantoin and dimethylhydantoin. The halogenated hydantoin compositions used to make the forms can also include additives such as solubility modifiers, compaction aids, fillers, surfactants, dyes, fragrances, dispersants, lubricants, mold releases, detergent builders, corrosion inhibitors, chelants, stabilizers, biocides, bromide sources, or oxidizing halogen compositions. The present invention is also the product which is made via the melt extrusion method. The invention also is a method of obtaining an improved feedstock via melt extrusion and the improved feedstock product. This improved feedstock product can be used for making forms by compaction.

20 Claims, No Drawings

5,750,061

HALOHYDANTOIN FORMS PRODUCED BY MELT EXTRUSION AND METHOD FOR MAKING

This application is a continuation-in-part application of U.S. application Ser. No. 08/554,476 filed Nov. 7, 1995, now abandoned.

BACKGROUND OF THE INVENTION

A distinct need exists for halogenated hydantoins in the form of high integrity granules, pellets and shaped forms, such as tablets, briquettes, and the like. These halohydantoin forms are useful in a variety of applications, such as bleaching, dishwashing, toilet bowl disinfection, and water treatment applications such as swimming pools, cooling water systems, and spas.

"High integrity" refers to solid products having a predetermined shape, which are hard, shape-retentive, and dust-free. Dust-free products are desirable because halogen donor compounds are irritating in nature. Furthermore, high dusting intensifies the halogen odor associated with these compounds, which is also irritating.

Halogenated derivatives of dimethylhydantoin are used in a variety of applications, such as swimming pool sanitizers (bromochloro-dimethylhydantoin) and bleaching (dichlorodimethylhydantoin). These halogenated dimethylhydantoins are fine, dusty powders which are difficult to obtain in solid forms. In the past, compaction has been suggested (see U.S. Pat. No. 4,242,216 issued to Daugherty et al.); however, many of the compounds require binders in order to compact well and some compounds do not compact at all. The use of binders to produce a commercial form of halodimethylhydantoin increases costs, and can require additional processing steps, e.g., a blending operation. Moreover, the binders do not alleviate the dust problem to the degree of the present invention. Many of the forms made by compaction are dusty and friable, and lack true integrity.

Briquettes, which are useful for water treatment, can be made by compaction. However, applications such as toilet cleaning require the halohydantoin to be in tablet form and the problems of producing larger forms by compaction techniques are increased in this form. Further, halogenated hydantoins for pool disinfection need to be in a different form because of the high dissolution rate of the compacted briquettes. The forms necessary for pool disinfection also cannot be made by compaction.

The production of forms by melt techniques (i.e., casting a molten material into a form, solidifying the material, and discharging the product by conventional means) is well known in other industries, such as candy making. Melt techniques provide particular advantage in the making of forms in that virtually any form of any size can be made, requiring only a mold of the specific size and shape, and that only limited by the creativity of the designer. "Designer" forms that might incorporate a logo or specific shape are possible. In some instances, the mold itself may serve as a dispenser for the compound, e.g., institutional dishwashing applications.

None of the traditional active halogen compositions (i.e., those based on cyanuric acid, succinimide, dimethylhydantoin, or the inorganics) are good candidates for melt techniques of shaping because the melt temperatures of the compounds are high (>100° C.) and very close to decomposition temperatures. However, halogenated methylethylhydantoin is an excellent candidate for melt techniques because of its low melt range and the great differential between its melt temperature and decomposition temperature. It has been found that, when halogenated methylethylhydantoin is mixed with halogenated dimethylhydantoin, the mixture can be shaped via melt techniques. The low melting methylethylhydantoin derivatives serve to disperse unmelted components to give the overall mix flow properties. See U.S. Pat. No. 4,560,766 issued to Girard et al.

The melt technique set forth in Girard et al. and used in the art for halohydantoins consists of a melt pot with a feed to a molding system. This system has several disadvantages. For one, it is very difficult to uniformly heat melt pots of halohydantoin, due to poor heat transfer in powders of this nature. In order to melt the material enough so that flow is established, the material near the heat source will necessarily be heated to a higher temperature than the material in the middle of the pot.

Moreover, while these halohydantoins have a rather large temperature differential between their melt temperature and their decomposition temperature, some breakdown and loss of material does occur in the melt pot technique when the material is left at the required high temperatures for too long. The breakdown of the material is undesirable for a number of reasons. For one, the fumes which will result from the breakdown are toxic. Further, the breakdown of the material can lead to a less pure and less effective compound.

Further, the halohydantoin material being heated in the melt pot will have a long heat history. When making a mold using this technique, more halohydantoin than is needed in the form is cooled and hardened. This means that the extra material has been repeatedly melted and cooled, in an effort not to waste the halohydantoin. However, after several times, the halohydantoin will break down and be unsatisfactory for use.

Finally, using this melt pot technique, hardened residue will often be left in the melt pot after the molding which requires extensive clean-up.

BRIEF DESCRIPTION OF THE INVENTION

It has been unexpectedly found that the method of melt extrusion, normally used in plastic applications, can be used to make halohydantoin forms and avoids the problems associated with conventional melt techniques. For example, unlike traditional melt techniques, melt extrusion techniques melt only the discrete, exact amount of material needed for the mold. Also, the material is subjected to elevated temperatures for only short periods of time due to large surface area contact with the material in an extruder. Moreover, a large change in temperature is not required to achieve the desired melt. Further, because melt extrusion techniques can cause materials to flow that are not readily flowing, only partial melting of the material is necessary. This reduces heat input.

The use of this technique for molding halohydantoins is quite novel and produces unexpected advantages. As noted previously, melt extrusion techniques are not normally used with these systems. In fact, although the Girard et al. patent issued almost ten years ago, no one has applied melt extrusion techniques to produce forms of halohydantoins. The resulting halohydantoin forms made by the melt extrusion process are dust-free, of high integrity, and stronger than forms made by conventional commercial methods.

An additional advantage of extrusion techniques is that additives can be formulated into the halohydantoin at the extruder itself because of the ability of the extruder to mix materials, particularly with twin screw equipment. There is no need for pre-blending equipment and, thus, cost and processing benefits are realized.

The present invention relates to the production of a solid halogenated hydantoin product by extruding a melt or a partial melt of the halohydantoin, cooling the extrudate to solidify the halohydantoin, and recovering the solid product. This process can be used to produce a variety of halohydantoin forms.

One embodiment of the invention relates to the production of halohydantoin forms by extruding a melt or partial melt of the halohydantoin into a mold of a predetermined size and shape, cooling the mold to solidify the halohydantoin, and recovering the solidified form from the mold in traditional techniques. Alternatively, the mold may serve as a dispenser for the chemical in its final application. Any form that can be produced in a mold or a die can be produced by this method, including tablets, pucks, pastilles, briquettes, pellets, granules, and so-called "designer" forms such as Christmas ornaments.

Another embodiment of the invention relates to a method of making granules of halohydantoin by extruding a melt or partial melt of the halohydantoin into sheets, cooling the sheets to solidify the halohydantoin, and grinding the sheets to obtain granules.

A further embodiment of the invention is a method for making pellets of halohydantoin by extruding a melt or partial melt of the halohydantoin through a die or screens to form strands, which are subsequently cut by conventional techniques into pellets, and cooling the resulting pellets.

A further embodiment of the invention is a method for producing an "agglomerate" from the original dusty powder by subjecting the powder to sufficient heat in an extrusion process to melt only a small portion of the powder (the melt acting as a "binder"), extruding the mix, and recovering the agglomerate by conventional means. This product has much better handling characteristics and minimal dust compared to the original powder, and would serve as a more efficient feedstock for traditional compaction processes used to make large forms, i.e., tablets for automatic toilet bowl applications. In a preferred embodiment, the extruder used in this method is a twin screw extruder.

The invention also relates to the solid halohydantoin product produced by the methods described above, including forms, granules, pellets, and feedstocks.

In a further embodiment of the invention, this extrusion technique can be applied to compositions containing the halohydantoins along with additives.

Another embodiment of the present invention are the extruded solid halogenated hydantoin products comprised of halohydantoins alone or with an additive.

DETAILED DESCRIPTION OF THE INVENTION

The halohydantoin compounds contemplated for use in this invention are described in U.S. Pat. No. 4,560,766, which is hereby incorporated by reference. These halohydantoin compounds have methylethylhydantoin (MEH) as a sole constituent or are an admixture of MEH and a halogenated dimethylhydantoin (DMH).

The halogenated methylethylhydantoin for use in this invention has the following structure:

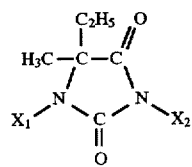

wherein $X_1$ and $X_2$ may be the same or different and are chlorine and bromine.

The halogenated dimethylhydantoins for use in this invention have the following structure:

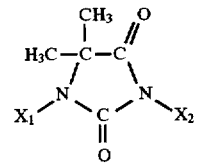

wherein $X_1$ and $X_2$ may be the same or different and are chlorine and bromine.

Halogenated MEH compounds, as compared to their corresponding halogenated DMH compounds, have significantly different thermal properties. One such property is the temperature differential between the melting point and the decomposition temperature of halogenated MEH compounds. These MEH compounds melt from about 60° to 70° C., whereas they decompose from about 150° to 170° C. This large temperature differential allows these compounds to be melted and formed without decomposing.

Further, mixtures of the dihalo DMH and MEH have the melt characteristics of the MEH derivatives such that fluid systems, consisting of unmelted dispersed solids in a molten medium, can be formed at low temperatures. Temperatures significantly below the thermal decomposition point of the mix are utilized.

Table 1 shows a range of products with melt and decomposition data. The products are listed in terms of their makeup relative to DMH, MEH and bromine (moles). For example, Dantobrom® is—0.8 DMH+0.2 MEH+0.5 NaBr and is thus referred to as product "8-2-5". Since each molecule of the hydantoin final product contains 2 moles of halogen, the moles of chlorine in each final product is 2.0 minus the moles of NaBr added.

Each of the products listed in Table 1 is made by first mixing MEH and DMH. The composition is then halogenated using conventional techniques. Two (2) moles of chlorine are added to every composition. If a bromochlorohydantoin or dibromohydantoin is desired, bromine, in the form of NaBr, is added in the desired molar amount. In a simple oxidation/reduction reaction, the chlorine oxidizes the bromine in the NaBr to Br$^+$, which then halogenates the DMH and MEH. Since each product has two moles of halogen, the remainder is halogenated by chlorine.

For example, in making Dantoin® 5-5-5, 0.5 mole of NaBr and 2.0 moles of chlorine are used to halogenate the MEH and DMH. The chlorine (0.5 mole) oxidizes the 0.5 mole of NaBr to Br$^+$, which halogenates the DMH/MEH, and the remaining chlorine (1.5 moles) halogenates the MEH/DMH. Thus, the final product contains 1.5 moles of chlorine and 0.5 mole of bromine. No NaBr is added to make the dichlorohydantoins. Two moles of NaBr are added to make the dibromohydantoins. While 2 moles of chlorine are also added to make the dibromohydantoins, all of the chlorine is used to convert the 2 moles NaBr to Br$^+$.

TABLE 1

| GENERAL CLASS | PRODUCT MAKEUP | | | MELT RANGE[1], °C. | DECOMPOSITION °C. |
|---|---|---|---|---|---|
| | DMH | MEH | Br | | |
| (A) DICHLOROHYDANTOINS | | | | | |
| DCDMH | 1.0 | 0.0 | 0.0 | 132–145 | 191 |
| DCMEH | 0.0 | 1.0 | 0.0 | 52–64<br>60–64[2] | 170 |
| Dantochlor® Dantoin® | 0.8 | 0.2 | 0.0 | 40–122 | 150 |
| • 5-5-0 | 0.5 | 0.5 | 0.0 | 53–95 | 170 |
| • 6-4-0 | 0.6 | 0.4 | 0.0 | 54–100[2]<br>42–119 | |
| • 7-3-0 | 0.7 | 0.3 | 0.0 | 40–130 | |
| (B) BROMOCHLOROHYDANTOINS | | | | | |
| Dantobrom® Dantoin® | 0.8 | 0.2 | 0.5 | 50–142 | 180 |
| • 5-5-5 | 0.5 | 0.5 | 0.5 | 54–110<br>65–121[2] | 180 |
| • 6-4-5 | 0.6 | 0.4 | 0.5 | 53–132 | |
| • 7-3-5 | 0.7 | 0.3 | 0.5 | 53–146 | |
| BCDMH | 1.0 | 0.0 | 1.0 | 158–165[2] | 160 |
| BCMEH Dantoin® | 0.0 | 1.0 | 1.0 | 74–79 | 148 |
| • 6-4-10 | 0.6 | 0.4 | 1.0 | 60–160 | Not available |
| • 7-3-10 | 0.7 | 0.3 | 1.0 | 57–170 | Not available |
| Dantobrom® BTB Dantoin® | 0.0 | 1.0 | 1.5 | 57–91<br>79–98[2] | 144 |
| • 5-5-15 | 0.5 | 0.5 | 1.5 | 79–165[2] | 144 |
| (C) DIBROMOHYDANTOINS | | | | | |
| DBDMH | 1.0 | 0.0 | 2.0 | ←179° C.[2] Decomp → | |
| DBMEH Dantoin® | 0.0 | 1.0 | 2.0 | 117–119[2] | 148 |
| • 8-2-20 | 0.8 | 0.2 | 2.0 | 158–180[2] | 177 |

[1]Melt range data based on differential scanning calorimetry.
[2]Capillary Melt Data The temperatures the halohydantoin compounds begin to melt (measured in most cases by differential scanning calorimetry which provides a clearer picture of early melt phenomena) in Table 1 are the lowest temperatures in the melt ranges shown. The data in Table 1 show that, with the exception of the dibromo derivatives, products containing greater than or equal to 20% MEH in the hydantoin makeup have differences between start of melt temperatures and decomposition temperatures greater than or equal to 65° C. and typically 70°–100° C. Halohydantoins with differences greater than 60° C., preferably greater than 70° C., between their start of melt and decomposition temperature can be used in the method of the present invention.

Halohydantoins with no more than 95 mole % of DMH and at least 5 mole % MEH can be used in this invention, with 0 to 90 mole % DMH and 10 to 100 mole % MEH being preferred. The most preferred halohydantoins used in this invention contain 0 to 80 mole % DMH and 20 to 100 mole % MEH. Halohydantoins made of 50 mole % DMH and 50 mole % MEH are preferred for melt extrusion of molded forms and granules. Halohydantoins made of 80 mole % of DMH and 20 mole % of MEH are preferred for making pellets. Halohydantoins made of no more than 95 mole % of DMH and at least 5 mole % MEH are preferred for making agglomerate.

Halogenated MEH compounds can be prepared as described in U.S. Pat. No. 4,560,766 or, alternatively, are available commercially from Lonza Inc., Fair Lawn, N.J., such as Dantobrom® BTB (MEH with 3:1 active bromine to chlorine).

The mixtures of halo MEH and halo DMH used in this invention can be made by mixing DMH and MEH in a predetermined quantity prior to halogenation. Mixtures can also be prepared in situ from the corresponding ketones, e.g., acetone and methylethylketone, using the Bucherer-Berg Synthesis, and then halogenating the product. Methods for obtaining these mixtures of halo MEH and DMH are set forth in U.S. Pat. No. 4,560,766. Alternatively, mixtures of halo MEH and DEH are available from Lonza Inc., under such trade names as Dantoin® 5-5-0 (⁵⁰⁄₅₀ molar ratio of MEH to DEH, all chlorine) and Dantoin® 5-5-5 (⁵⁰⁄₅₀ molar ratio of MEH to DEH with 3:1 active chlorine to bromine).

Furthermore, the compositions used in the invention also include a mixture of halohydantoins with additives. Examples of additives which can be used in the present invention include solubility modifiers, compaction aids, fillers, surfactants, dyes, fragrances, dispersants, lubricants, mold releases, detergent builders, corrosion inhibitors, chelants, stabilizers, biocides, bromide sources, and oxidizing halogen compositions. The additives provide an additional function or serve as a processing aid in the preparation of the form. The only requirement is that the material be compatible with the halohydantoin composition.

Products made of halohydantoins with no more than 95 mole % of DMH, at least 5 mole % MEH, and certain additives in the amounts given below are a further embodiment of the present invention. Any of the additives listed above could be used in these products, with solubility modifiers, compaction aids, fillers, fragrance, mold releases, and oxidizing halogen compositions being the most preferred.

Solubility modifiers which may be added to the halohydantoin described herein include, for example, sodium bicarbonate, aluminum hydroxide, magnesium oxide, barium hydroxide, and sodium carbonate. See U.S. Pat. No. 4,537,697. Solubility modifiers can be used in the compositions in an amount ranging from 0.5 to 50% by weight.

Examples of compaction aids include inorganic salts comprised of lithium, sodium, potassium, magnesium and calcium cations associated with carbonate, bicarbonate, borate, silicate, phosphate, percarbonate and perphosphate. See U.S. Pat. No. 4,677,130. Compaction aids can be used in the compositions in an amount ranging from 0.5 to 50% by weight.

Fillers added to the halohydantoins include, for example, inorganic salts, such as combinations of lithium, sodium, potassium, magnesium and calcium cations with sulfate, and chloride anions, as well as other inorganics such as clays and zeolites. Fillers are used in the compositions to reduce product costs and can be added in an amount ranging from 1 to 50 % by weight.

Examples of surfactants include Aerosol OTB (sodium dioctyl sulfosuccinate), disodium lauryl sulfosuccinate, sodium lauryl sulfoacetate, and sodium cocoylisethionate, as well as other sulfonates. Surfactants are used in the compositions to enhance cleaning performance and can be added in an amount ranging from 0.5 to 40% by weight.

Dyes and pigments can be added to the compositions in an amount of 0.1 to 10 % by weight. Examples of dyes and pigments are copper phthalocyanine tetrasulfonic acid tetra sodium salt, all derivatized and underivatized phthalocyanines such as Pigment Green 7, Pigment Blue 15, and Pigment Blue 86, as well as inorganic pigments, such as lazurite.

Fragrances can also be used as additives and can be added in an amount ranging from 0.1 to 10% by weight.

Dispersants may be added to inhibit scale deposition in treated waters in an amount ranging from 0.1 to 20% by weight. Examples of dispersants include all polyacrylate based polymers including secondary and tertiary polymers and some phosphonate dispersants, such as Bayhibit S®, 2-phosphono-1,2,4-butanetricarboxylic acid tetra-Na salt (PBTC).

Lubricant/mold releases which may be added to the hydantoin include Acrawax® C, magnesium, calcium, and sodium stearate. These lubricant/mold releases are added to the compositions in an amount ranging from 0.1 to 20% by weight.

Detergent builders are added to the compositions in order to enhance cleaning performance. An example of a detergent builder is sodium tripolyphosphate. They are added in an amount ranging from 1 to 50% by weight.

Chelants are used in the compositions to sequester metal ions and enhance hard water performance and are added in an amount ranging from 1 to 50% by weight. Examples of chelants include sodium gluconate, ethylene diamine tetraacetic acid (EDTA), citric acid, and sodium nitrilotriacetate (NTA).

N-hydrogen stabilizers are added to the compositions in order to enhance tablet stability and increase additive compatibility and are added in an amount ranging from 0.5 to 20% by weight. Examples of N-hydrogen stabilizers include dimethylhydantoin, 5,5-dimethylhydantoin (DMH), 5,5-methylethylhydantoin (MEH), cyanuric acid, sulfamic acid, sulfonamide, sulfamates, glycoluril, and succinimide.

Examples of inorganic biocides which may be added to the compositions include molybdates, copper sulfate, selenates, tungstates, and chromates. See U.S. Pat. No. 4,995,987. These biocides are added in an amount ranging from 0.1 to 10% by weight.

Bromide sources may be added to provide biocidal bromide ($Br^+$) in the presence of active chlorine. Bromide sources may be added in an amount ranging from 1 to 30% by weight. Examples of bromide sources include sodium bromide and potassium bromide.

Oxidizing halogen compositions may be added to optimize product performance by optimizing Br/Cl and DMH/MEH ratios. An example of an oxidizing halogen composition is bromochlorodimethylhydantoin. They are added to the compositions in an amount ranging from 1 to 95 % by weight.

It has been unexpectedly found that melt extrusion processing is an ideal technique for exploiting the melting properties of the halohydantoin compounds and obtaining halohydantoin forms without the problems of the prior known processes.

The halohydantoin powder of choice is introduced into the extruder. The extruder is zone-heated and controlled to achieve the specified temperature for the particular halohydantoin. By using this technique, only small quantities of materials are subject to heating and for only limited periods. Other advantages of using extruders are the high throughput and the consistency of output. The ability to blend additives at the extruder, thus eliminating pre-blending equipment, is a further advantage.

A single extruder can provide wide flexibility in producing forms. The molten slurry extrudate can be directly flowed into molds for tablets, briquettes, or other shapes, including "designer" shapes. Alternatively, the slurry can be extruded to sheets for subsequent granulation or through dies for pelletization. Any extruder used in a commercial setting can be used for this invention. It has been found that a screw extruder, either single or twin, is particularly useful in practice of the method of the present invention.

A system for cooling and solidification of the product is required. Belt systems, used for flaking operations, can be used. Other systems known in the art can be used in this method.

Any method known in the art can be used for recovering the form from the mold. Moreover, techniques known in the art for granulation, cutting extrudate, and cooling can be used in this method for obtaining pellets and granules.

The following examples are illustrative of the present invention; however, it will be understood that the invention is not limited to the specific details set forth in the examples. Examples 1–7 use a single screw extruder and Examples 8–10 use a semi-commercial twin screw extruder in the methods described therein.

EXAMPLE 1

A $50/50$ mixture of methylethylhydantoin and dimethylhydantoin, all chlorine halohydantoin (melt range ~53°–95° C. DSC) (Dantoin® 5-5-0 powder, Lonza) was fed through the hopper of an extruder (C. W. Brabender, Electronic Plasti-Corder Torque Rheometer, Type EPL-V302, with Brabender single screw extruder, 3-zone, Type 2523 with a stainless steel screw 25:1 L/D, 2:1 compression ratio and rod die with no insert (thermal collar attached), screw speed—60 RPM). The following settings were made on the extruder: Zones 1, 2, 3: 70° C.; Die: 65° C. (readout); and melt temperature: 64°–65° C. The approximate residence time of the halohydantoin in the extruder was 30 to 40 seconds. The output was approximately 62 grams/minute.

The extrudate had the consistency of light, well-mixed pancake batter and was collected in the following molds:

a) 70 mm smooth aluminum weight dishes (approximately 100 grams);

b) small ice cube trays, ¾"×¾" (approximately 16 grams);

c) small aluminum cups 1⅛"×⅞", (approximately 45 grams); and d) various plastic molds of animals, trees and Christmas decorations ("designer" forms).

The material was also "spilled" into trays for eventual break-up and screening to form granules.

After cooling to room temperature, the molded products were recovered by conventional laboratory techniques. For example, 100 gram tablets were simply popped out of the 70 mm aluminum dishes by exerting finger pressure on the outside bottom center of the dish. The recovered tablet maintained full integrity (hard, uniform surface) and was completely dustless. Measurement of the force required to fracture the tablet was performed by contacting a vertical blade across the face of a suspended tablet (Instron® Instrumentation). The force required to fracture the tablet was 125 lb. as opposed to an average of 83 lb. for commercially produced tablets of similar weight and shape.

The commercial tablets used for comparison are currently made by any number of standard compaction techniques and equipment, such as rotary tablet presses, in which a powder or granule is injected into a mold and subjected to compression forces of approximately 10,000 pounds.

EXAMPLE 2

A $50/50$ mixture of methylethylhydantoin and dimethylhydantoin, 3:1 chlorine to bromine halohydantoin (melt range ~54°–110° C., DSC) (Dantoin® 5-5-5 powder, Lonza) was processed as described in Example 1.

The 100 gram tablets obtained maintained full integrity and were dustless. Breaking of the tablets required 135 lb. force.

EXAMPLE 3

A halohydantoin comprising 100% methylethylhydantoin with 3:1 active bromine to chlorine (melt range 57°–91° C., DSC) (Dantobrom® BTB powder, Lonza) was processed as described in Example 1, except the extruder had the following settings: Zones 1, 2, 3: 70°, 75°, 70° C., respectively; Die 80° C.; melt temperature: ~81° C.

The output had the consistency of thick pancake batter and was discharged onto a tray for grinding and conversion to granule products. The resolidified mass had good integrity and ground readily with minimal dust.

EXAMPLE 4

Dantobrom® BTB used in Example 3 was processed as described in Example 1, except the extruder had the following settings and die: Zones 1, 2, 3: 70° C.; Die: 65° C.; melt temperature: 65° C.; and a 3/16" plug die. A strand of extrudate was produced which had good integrity at the die face, and which could be cut at the die face directly into pellets. The pellets hardened rapidly into handleable form.

EXAMPLE 5

A dry blend of 70% Dantoin® 5-5-0, 20% dimethylhydantoin (stabilizer), and 10% copper phthalocyaninetetrasulfonic acid, tetra sodium salt dye was processed and extruded as described in Example 1, with die and melt temperature at approximately 70° C. A flowing melt was produced which was readily cast into 30 and 100 gram molds. The cooled tablets were blue, hard, non-dusting forms.

EXAMPLE 6

Dantochlor®, an 8-2-0 composition, was fed into the extruder as described in Example 1. Zones 1, 2, and 3 were 70°, 65°, and 60° C., respectively; die: 55° C.; melt temperature: 61° C. A strand-like extrudate was obtained which on cooling had an agglomerated/granular appearance. It was readily broken into a granular powder with good flow properties and minimal fines.

EXAMPLE 7

Various additives were tested for their compatibility with halohydantoins for use in melt extrusion. Mixtures were prepared comprising 90 % by weight of a halohydantoin and 10% by weight of the additive. The halohydantoins used were either Dantoin® 5-5-0 or Dantoin® 5-5-5. The specific additives are listed in Table 2, column 3 and the category of the additive is listed in Table 2, column 2.

TABLE 2

| Halohydantoin | Additive Category | Additive Example |
|---|---|---|
| 5-5-0 | Solubility Modifier | Aluminum Hydroxide |
| 5-5-0 | Compaction Aids | Sodium Bicarbonate |
| 5-5-0 | Filler | Sodium Sulfate |
| 5-5-0 | Surfactant | Aerosol ® OTB |
| 5-5-0 | Dye | Sulfonated copper phthalocyanine |
| 5-5-0 | Dispersant | Polyacrylic acid |
| 5-5-0 | Dispersant | Bayhibit ® S |

TABLE 2-continued

| Halohydantoin | Additive Category | Additive Example |
|---|---|---|
| 5-5-0 | Lubricant/Mold release | Acrawax ® C |
| 5-5-0 | Detergent Builder | Sodium Tripolyphosphate |
| 5-5-0 | Corrosion Inhibitor | Sodium Silicate |
| 5-5-0 | Corrosion Inhibitor | Sodium Benzoate |
| 5-5-0 | Chelant | Sodium Gluconate |
| 5-5-0 | Stabilizer | Dimethylhydantoin |
| 5-5-0 | Biocide | Copper Sulfate |
| 5-5-0 | Bromide Source | Sodium Bromide |
| 5-5-0 | Oxidizing halogen composition | BCDMH |
| 5-5-5 | Solubility Modifier | Aluminum Hydroxide |
| 5-5-5 | Filler | Sodium Sulfate |
| 5-5-0 | Solubility Modifier | Aluminum Hydroxide |
| 5-5-5 | Dispersant | Polyacrylic acid |

The mixtures were heated to a range of 85° to 95° C. in an oil bath. Upon melting, the mixture was poured into a small hexagonal plastic mold and allowed to cool. In each case, there was no visual discoloration and the forms were solid and dust-free.

EXAMPLE 8

Dantochlor®, an 8-2-0 composition, was fed through the hopper of a Werner/Pfleiderer ZSK-30, Co-rotating Twin Screw Extruder, set up with four heating zones, a die and die face plate. The screw elements consisted of conveying, kneading, and pumping designs. The following settings were made on the extruder: Zone 1: 40° C.; Zones 2, 3, 4: 50° C.; die: 50° C. (readont); and die face plate: 60° C. Dantochlor® was fed at a rate of 50 lbs/hr.

The extrudate had a uniform strand-like consistency with an excellent integrity. The die hole was 3.5 mm. Addition and operation of a knife blade pelletizer at the die face resulted in the formation of pellets in handleable, packageable forms. The size of the pellets could be modified by adjusting the speed of the pelletizer. The pellets cooled rapidly on the conveyor belt.

EXAMPLE 9

Dantobrom®, an 8-2-5 composition, was fed into the extruder as described in Example 8; Zones 1, 2, 3, and 4 were 35°, 45°, 50°, and 55° C., respectively; die: 65° C.; die face plate: 75° C. Pellets with excellent integrity were obtained.

EXAMPLE 10

Dantochlor® BTB used in Example 3 was processed as described in Example 8, except the extruder had the following settings, die and die face plate temperatures: Zone 1: 55° C.; Zones 2–4: 60° C.; die: 65° C.; die face plate: 60° C. The extrudate produced gave a readily formed product.

We claim:

1. A method for the production of a solid halogenated hydantoin product containing from 5 to 20 mole % of methylethylhydantoin and from 80 to 95 mole % of dimethylhydantoin, comprising:

(a) extruding said halogenated hydantoin under conditions sufficient to only partially melt said halogenated hydantoins for a residence time of not greater than 40 seconds;

(b) cooling said extrudate to solidify said halogenated hydantoin; and (c) recovering a substantially dust-free solid product.

2. The method of claim 1, wherein said methylethylhydantoin and dimethylhydantoin are halogenated with either chlorine alone or chlorine and bromine.

3. The method of claim 1, wherein said composition contains at least 10 mole % of methylethylhydantoin and no more than 90 mole % of dimethylhydantoin.

4. A solid halogenated hydantoin product containing at least 5 mole % of methylethylhydantoin and not more than 95 mole % of dimethylhydantoin made by:

(a) extruding said halogenated hydantoin under conditions sufficient to only partially melt said halogenated hydantoins for a residence time of not greater than 40 seconds;

(b) cooling said extrudate to solidify said halogenated hydantoin; and (c) recovering a substantially dust-free solid product.

5. A method for making a halogenated hydantoin feedstock for compaction containing at least 5 mole % of methylethylhydantoin and not more than 95 mole % of dimethylhydantoin, comprising extruding a dusty powder of said halogenated hydantoin under conditions sufficient to only partially melt said halogenated hydantoins for a residence time of not greater than 40 seconds to obtain an agglomerate.

6. The method of claim 1, wherein said solid halogenated product also contains at least one of the following additives: a solubility modifier, a compaction aid, a filler, a surfactant, a dye, a fragrance, a dispersant, a lubricant, a mold release, a detergent builder, a corrosion inhibitor, a chelant, a stabilizer, a biocide, a bromide source, and an oxidizing halogen composition.

7. The method of claim 1, wherein said solid product is a tablet, briquette, granule, pellet, or dispenser.

8. The method of claim 1, wherein said halogenated hydantoin is extruded through a screw extruder.

9. The method of claim 8, wherein said screw extruder is a single screw extruder or a twin screw extruder.

10. The method of claim 1, wherein said melt or partial melt of said halogenated hydantoin is extruded into a mold of predetermined size and shape, cooled, and recovered from said mold.

11. The method of claim 1, wherein said melt or partial melt of said halogenated hydantoin is extruded into sheets, and said sheets are cooled and ground to obtain granules of halogenated hydantoin.

12. The method of claim 1, wherein said melt or partial melt of said halogenated hydantoin is extruded through a die, cut into pellets, and cooled.

13. The product of claim 4 wherein the partial melt of the solid halogenated hydantoin product contains a dusty powder and the recovered solid product is an agglomerate.

14. The product of claim 4, wherein said melt or partial melt of said halogenated hydantoin is extruded into a mold of predetermined size and shape, cooled, and recovered from said mold as a solid product.

15. The product of claim 4, wherein said melt or partial melt of said halogenated hydantoin is extruded into sheets, said sheets cooled and ground into granules.

16. The product of claim 11, wherein said melt or partial melt of said halogenated hydantoin is extruded through a die, cut into pellets and cooled.

17. The product of claim 11, wherein said product also contains at least one of the following additives: a solubility modifier, a compaction aid, a filler, a surfactant, a dye, a fragrance, a dispersant, a lubricant, a mold release, a detergent builder, a corrosion inhibitor, a chelant, a stabilizer, a biocide, a bromide source, and an oxidizing halogen composition.

18. The method of claim 5, wherein said methylethylhydantoin and dimethylhydantoin are halogenated with chlorine alone or chlorine and bromine.

19. The method of claim 5, wherein said composition contains at least 10 mole % of methylethylhydantoin and no more than 90 mole % of dimethylhydantoin.

20. The method of claim 5, wherein said halogenated hydantoin feedstock also contains at least one of the following additives: a solubility modifier, a compaction aid, a filler, a surfactant, a dye, a fragrance, a dispersant, a lubricant, a mold release, a detergent builder, a corrosion inhibitor, a chelant, a stabilizer, a biocide, a bromide source, and an oxidizing halogen composition.

* * * * *